Universit ed States Patent [19]

Greth

[11] 4,039,570
[45] Aug. 2, 1977

[54] PROCESS FOR THE PRODUCTION OF SUCCINYLOSUCCINIC DIESTER

[75] Inventor: Erich Greth, Visp, Switzerland

[73] Assignee: Lonza Ltd., Gampel, Switzerland

[21] Appl. No.: 575,371

[22] Filed: May 7, 1975

[30] Foreign Application Priority Data

May 7, 1974 Switzerland .................. 006166/74

[51] Int. Cl.$^2$ ............................................. C07C 69/95
[52] U.S. Cl. ................................................ 260/468 K
[58] Field of Search .................................... 260/468 K

[56] References Cited

U.S. PATENT DOCUMENTS

| | | | |
|---|---|---|---|
| 3,775,467 | 11/1973 | Greth | 260/483 |
| 3,803,209 | 4/1974 | Greth | 260/468 K |
| 3,914,281 | 10/1975 | Greth | 260/468 K |

Primary Examiner—Lorraine A. Weinberger
Assistant Examiner—Michael Shippen
Attorney, Agent, or Firm—Fisher, Christen & Sabol

[57] ABSTRACT

A process for the production of succinylosuccinic acid diester. The process includes reacting a γ-haloacetoacetic ester with a strong base. The reaction is conducted in the presence of at least one dispersing agent and an aqueous buffer solution of at least one inorganic salt at a pH of 8 to 10. The pH is kept constant during the reaction by the addition of a strong base as needed. The reaction is conducted at a temperature between $-10°$ and 10° C. and preferably between $-2°$ and 0° C. The succinylosuccinic acid diester can be isolated by any convenient method such as filtering or centrifuging it from the reaction solution.

11 Claims, No Drawings

PROCESS FOR THE PRODUCTION OF SUCCINYLOSUCCINIC DIESTER

BACKGROUND OF THIS INVENTION

1. Field of this Invention

This invention relates to a process for the production of succinylosuccinic acid diester from γ-haloacetoacetic ester in a water medium by means of at least one strong base.

2. Prior Art

Succinylosuccinic acid diester has been produced by reaction from γ-chloroacetoacetic ester in water by reaction with sodium phenolate; in that case, a yield of only 58 percent was obtained (Bull. Soc. Chim. France 29, 192, pp. 402-6).

Succinylosuccinic acid diester has been produced from succinic acid diethyl ester (as a starting material). In that case the succinic acid diethyl ester was reacted with sodium ethylate. The highest yield that was achieved by that process was around 80 percent (U.S. Pat. No. 3,024,268). The main disadvantage of that process, however, is that the isolation of the resultant succinylosuccinic acid diester is exceedingly cumbersome, difficult and time consuming. Furthermore, large quantities of solvent are needed in that process.

Succinylosuccinic ester have been prepared from ethyl succinate and Na using a double Claisen reaction. Whitmore, F. C., "Organic Chemistry", 2nd Ed. (1951), p. 381. Succinylosuccinic esters have been produced by reacting $NaOC_2H_5$ and ethyl succinate. Whitmore, ibid, p. 708.

See also U.S. Pat. No. 3,803,209.

BROAD DESCRIPTION OF THIS INVENTION

It is the objective of this invention to produce succinylosuccinic diester from γ-halogenacetoacetic ester by means of a simple process in high yields. Other objects of this invention are set out herein or are obvious to one ordinarily skilled in the art from this specification, including the claims.

Applicant's U.S. Pat. No. 3,803,209 discloses producing succinylosuccinic acid diester from γ-haloacetoacetic ester in water by means of a strong base. The conversion of the γ-haloacetoacetic acid ester, in the patent, is carried out in an aqueous buffer solution of inorganic salts at a pH value of 8 to 10.

Applicant has found that the quantity of water needed for the reaction can be reduced to about one sixth and that the reaction time can be shortened considerable without any loss in yield resulting.

The process of this invention involves the production of succinylosuccinic acid diester. The process includes reacting γ-haloacetoacetic acid alkyl ester having the formula:

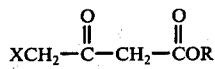

wherein X is a halogen atom and R is a lower alkyl group, with a strong base. The reaction is conducted in the presence of at least one dispersing agent and an aqueous buffer solution of at least one inorganic salt at a pH of 8 to 10. The pH is kept constant (i.e., within the recited range) during the reaction by the addition of a strong base as needed. The reaction is conducted at a temperature between −10° and 10° C. and preferably between −2° and 0° C. The succinylosuccinic acid diester can be isolated by any convenient method, such as, filtering or centrifuging it from the reaction solution. The product has a white to slightly yellowish color and as a purity of greater than 99 percent.

The succinylosuccinic diester can be used for the production of polymers and for the production of quinacridone dye stuffs.

DETAILED DESCRIPTION OF THIS INVENTION

The effect of the use of the dispersing agent is that the organic reaction components are finely distributed, and hence readily available, the reaction mixture and that the organic reaction components do not settle out on the walls of the reaction vessel or that the organic reaction components do not lead to pastelike, non-stirrable mixtures. Furthermore, by the use of the dispersing agent, an unexpected, significant increase of the yield is obtained.

The dispersing agent should be used in an amount between 0.01 and 10 percent, and preferably in an amount between 0.2 and 2 percent, based on the amount of γ-haloacetoacetic acid alkyl ester.

The dispersing agent can be an anionic, cationic or nonionic dispersing agent or can be a mixture thereof. Examples of useful dispersing agents are polyhydroxyethylcelluloses, fatty alcohol sulfates, alkyl sulfonates, alkylaryl sulfonates, alkylene oxide polymers, soaps, polyglycol ether or ester of fatty alcohols, fatty acids, fatty acid amides, fatty acid alkylol amides, alkylphenols or their sulfates thereof, quaternary ammonium compounds, quaternary phosphonium compounds and mixtures thereof.

Examples of cationic dispersing agents are the quaternized alkyloamine esters, such as, Avitex ML. Examples of nonionic dispersing agents are the alcohol/ethylene oxide adducts, such as, Merpol SE, Merpol OA and Merpol Hc.

Examples of anionic dispersing agents are the sodium salts of alcohol sulfates, such as, Duponol 80, Duponol WN, Duponol LS and Avitex C, amine salts of alcohol sulfates, such as, Duponol AM, Duponol EP and Duponol G, alcohol phosphates, such as, Zelec NE and Zelec NK, fluorinated phosphates, such as, Zonyl S-13, aliphatic sulfonates, such as, Petrowet R, Alkanol 189-S and Avitone T, and alkylaryl sulfonates, such as, Alkanol B, Neomerpin N and Merpentine.

The reaction is conducted at a temperature between −10° and 10° C. and preferably between −2° and 0° C.

The pH of the reaction solution during the reaction (conversion) must be retained between 8 and 10, preferably between 9 and 10, and most preferably at 9.5.

The required pH range during the reaction or conversion is assisted in being maintained by the use of an aqueous buffer solution, the buffer being comprised of at least one inorganic salt. Preferably the buffer is comprised of two inorganic salts or an inorganic salt and a strong inorganic base (e.g., NaOH). The preferred buffer is a mixture of $Na_2CO_3$ and $NaHCO_3$, being preferably used at a ratio of 0.5 to 1.5 moles of $Na_2CO_3$. When the buffer is a mixture of $NaHCO_3$ and NaOH, their ratio is preferably 1 mole of $NaHCO_3$ to 0.2 to 0.8 mole NaOH. An example of another useful buffer is a mixture of $Na_2B_4O_7$ and sodium hydroxide.

According to this invention, the γ-halogen acetoacetic acid alkyl ester is dispersed in an aqueous buffer solution of inorganic salts with a pH value of 8 to 10, and the strong base that is used up by the formation of acid is replaced during the reaction by the addition of more strong base. The addition of such strong base can be on a continuous, semi-continuous or batch basis. Effectively the pH of the reaction medium is measured during the reaction and the base is continuously replaced or replaced at short intervals according to the measure of the pH change, so that the pH is always held constant within the range of this invention. (The pH can be controlled during the reaction using known methods, for example, electrochemically.)

The strong base preferably should be a strong inorganic base. The strong base preferably should have a dissociation constant (k), in aqueous solutions, of at least $1 \times 10^{-3}$ and most preferably of at least $1 \times 10^{-2}$. Examples of such useful strong inorganic bases are: sodium hydroxide (most preferred); potassium hydroxide; barium hydroxide; and calcium hydroxide. Mixtures of strong bases can be used.

Useful γ-haloacetoacetic esters have the formula:

wherein R is an alkyl group of X is a halogen atom. R can be straight or branched chained.

As used herein X can be chlorine, bromine, iodine or fluoride, but chlorine is preferred.

Examples of useful γ-haloacetoacetic acid esters are: γ-chloroacetoacetic acid ethyl ester γ-chloroacetoacetic acid methyl ester, γ-chloroacetoacetic acid n-propylester, γ-chlororacetoacetic acid isoproply ester, γ-chloroacetoacetic acid n-butyl ester, γ-chloroacetoacetic acid isopentyl ester, γ-chloroacetoacetic acid n-hexyl ester, γ-chloroacetoacetic acid n-decyl ester, γ-chloroacetoacetic acid 4-methyl-1-heptyl ester, γ-bromoacetoacetic acid methyl ester, γ-bromoacetoacetic acid ethyl ester, γ-bromoacetoacetic acid n-propyl ester, γ-bromoacetoacetic acid n-hexyl ester, γ-fluoroacetoacetic acid ethyl ester and γ-iodoacetoacetic acid ethyl ester.

Succinylosuccinic acid diester is also termed succinosuccinic ester or 1,4-dicarbethoxy-2,5-diketocyclohexane or succinylosuccinic ester and has the following general formula:

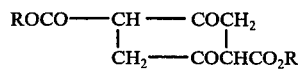

R is defined above and can be different lower alkyl groups.

The alcohol component of the starting ester correlates with the succinylosuccinic diester that is to be produced. The γ-haloacetic acid esters are usually prepared from an alcohol and γ-haloacetoacetic acid chloride.

R in the ester or diester formulas can be any alkyl group containing one to ten carbon atoms and can be a straight chain or branch chain alkyl group, but is preferably an alkyl group containing one to 4 carbon atoms and is most preferably methyl or ethyl. Other examples of useful alkyl groups which R can be are: n-propyl, isopropyl, n-butyl, isobutyl, n-pentyl, isopentyl, n-hexyl, n-heptyl, n-octyl, n-nonyl, n-decyl, neo-pentyl, 2,4-dimethyl-3-pentyl, 2-heptyl, 3-heptyl, 2-methyl-2-heptyl, 3-methyl-2-heptyl, 4-heptyl, 2,6-dimethyl- 4-heptyl, 4-ethyl-4-heptyl, 2-methyl-1-heptyl, 4-methyl-4heptyl, 3-methyl-1-heptyl, 4-propyl-4-heptyl, 4-methyl-1-heptyl, 2,2,3,3-tetramethyl butyl 2,3-dimethyl pentyl, 2,2,4-trimethyl pentyl, 2,4-dimethyl-3-ethyl-3-hexyl, 2-ethyl-hexyl, 2-butyl, t.-butyl, 2-methyl-1-butyl, 2-pentyl, 3-pentyl, 3-methyl-2-butyl, 2-methyl-2-butyl, 2-methyl-1-pentyl, 3-methyl-1-pentyl 4-methyl-1-pentyl, 2-ethyl-1-butyl, t.-amyl, 2,3-dimethyl-1-butyl, 2-hexyl, 3-hexyl, 3-methyl-2-pentyl, 2,2-dimethyl-3-butyl, 4-methyl-2-pentyl, 2,3-dimethyl-2-butyl, 2-methyl-3-pentyl, and 3-methyl-3-pentyl and 2-methyl-2-pentyl.

The succinylosuccinic acid diester can be isolated from the reaction solution by any conventional or convenient means such as filtering or centrifuging the reaction solution. The product is white to slightly yellowish in color and has a purity above 99 percent (determined by titration with tetrabutylammonium hydroxide in pyridine).

The succinylosuccinic acid diesters are used for the production of quinoacridone dyes and in the production of polymers.

By way of summary, this invention involves converting γ-haloacetoacetic acid alkyl ester in the presence of at least one dispersing agent in an aqueous buffer solution of at least one inorganic salt at a pH value of 8 to 10, whereby the pH is kept constant through the addition of a strong base during the reaction.

In the following examples and throughout the rest of the application, all parts, ratios, and percentages are on a weight basis unless otherwise stated or obviously so to one ordinarily skilled in the art.

EXAMPLE 1

15.25 gm. of sodium carbonate, 3.1 gm. of sodium bicarbonate and 0.300 gm of Natrosol 250 MXR (polyhydroxethyl cellulose) were dissolved in 130 ml of distilled water and were reacted at -2°C., while being stirred with 35.7346 gm. of distilledγ-chloroacetoacetic acid ethyl ester (content 97.79 percent, which corresponds to 34.9449 gm of a 100 percent product). After one hour, 5 ml of 7.2-N-caustic soda solution was added. This operation was repeated after 2, 3 and 4 hours. After 22 hours, the undissolved product was sucked off, was washed with 150 ml of water and 80 ml of methanol and was dried. 21.2950 gm of succinylosuccinic acid diethylester, having a melting point of 126.3°C., was obtained - this corresponded to a 78.3 percent yield.

EXAMPLE 2

6.9 gm, of sodium bicarbonate, 11.5 gm. of sodium carbonate and 0.35 gm. of Fenopon CO 436 (ammonium salt of a sulfate of an oxy-ethylated alkyl phenol) were dissolved in 120 ml. of water, were cooled to -2° C and were reacted, while being stirred with 35.9846 gm. of γ-chloroacetoacetic acid ethyl ester (content 99.02 percent, which corresponds to 35.6320 gm. of a 100 percent product). Then the pH of the reaction solution was kept at 9.5 through the addition of a total of 28.8 ml. of 7.2 N caustic soda solution with the aid of an automatically operating pH measuring instrument having a dosing capability. After 22 hours, the product was processed as in Example 1. 21.6637 gm. of succinylosuccinic acid diethyl ester was obtained-this corresponded to a 77.22 percent yield.

EXAMPLES 3 to 5

Example 2 was repeated three times. When Fenopon CO 436 was replaced with Natrosol 250 MXR, a yield of 77.06 percent resulted, with Tensofol AG (fatty alcohol sulfate), a yield of 73.04 percent resulted, and with Pluronic F 68 (ethylene-oxidepropyleneoxide-copolymer), a yield of 73.54 percent resulted. Examples 2 to 5 cannot be carried out without a dispersing agent, since deposits of organic material occur at the electrode when no dispersing agent is used and thus faulty measurements result.

EXAMPLE 6

Using the method of operation of Example 2, 13.8 gm. of sodium bicarbonate, 16.8 gm. of sodium carbonate and 9.0 gm. of Fenopon CO 433 (sodium salt of a sulfate of an oxy-ethylated alkyl phenol) were reacted with 144.04 gm. of γ-chloroacetoacetic acid ethyl ester (content 97.87 percent, which corresponds to 140.97 gm. of a 100 percent product). However the reaction was conducted at 10° C and at a pH of 9.75. The reaction was discontinued after 7 hours. 88.52 gm. of succinylosuccinic acid diethyl ester, having a melting point of 126.6° to 126.8°C., was isolated. The product yield was 80.7 percent.

EXAMPLE 7

13.8 gm. of sodium bicarbonate, 16.8 gm. of sodium carbonate and 1.2 gm. of Fenopon CO 433 (sodium salt of a sulfate of an oxy-ethylated alkyl phenol) were reacted in 250 ml of water (as in Example 2) with 72.62 gm. of γ-chloroacetoacetic acid ethyl ester (content 87.87 percent, which corresponds to 63.53 gm. of a 100 percent product). After 8 hours, at -2° C. and a pH of 9.5, the addition of caustic soda solution was discontinued the temperature was raised slowly to 20° C. After a total of 22 hours of reaction time, the product was processed, as in Example 1. 37.82 gm. of succinylosuccinic acid diethyl ester were obtained — this is a 76.5 percent yield.

EXAMPLE 8

Example 2 was repeated except that 13.8 gm. of sodium bicarbonate, 16.8 gm. of sodium carbonate and 1.7 gm. of trimethylbenzylammoniumhydroxide (as a 40 percent solution in methanol) were used. Using 72.45 gm. of γ-chloroacetoacetic acid ethyl ester (content 96.10 percent, which corresponded to 96.62 gm. of a 100 percent product), 45.00 gm. of succinylosuccinic acid diethyl ester was obtained. This corresponded to a 83.0 percent yield.

EXAMPLES 9 to 14

Example 2 was repeated six times using certain quaternary ammonium and phosphonium compounds. The yields were similar to the other examples.

| Example No. | Dispering Agent | Yield Percent |
| --- | --- | --- |
| 9 | triethylbenzylammoniumchloride | 79.4 |
| 10 | tetrabutylammoniumiodide | 80.1 |
| 11 | dioctyldimethylammoniumchloride | 82.6 |
| 12 | myristyldimethylbenzylammoniumchloride | 84.7 |
| 13 | tetraphenylphosphoniumbromide | 80.8 |
| 14 | methoxymethyltriphenylphosphonium-bromide | 76.5 |

EXAMPLE 15

19.30 gm. of sodium carbonate, 3.10 gm. of sodium bicarbonate and 0.20 gm. of Natrosol 250 MXR (Polyhydroxyethyl cellulose) were dissolved at ambient temperature in 150 ml of distilled water, were cooled to -2°C. and were reacted, while being stirred with 23.9310 gm. of technical γ-chloroacetoacetic acid ethyl ester (content 87.80 percent which corresponded to 21.0114 gm. of a 100 percent product). After 22 hours at -2° C., the succinylosuccinic acid diethyl ester which had been produced was sucked off, was washed with 150 ml of water and 50 ml of methanol and was dried for 16 hours at 80° C/20 torr. 12.6255 gm. of succinylosuccinic acid diethyl ester, having a melting point of 126.0° to 126.2° C, was obtained — this corresponded to a yield of 76.4 percent.

EXAMPLE 16

Example 15 was repeated without the addition of Natrosol 250 MXR - there was a yield of 67.5 percent of succinylosuccinic acid dietheyl ester. The use of the dispersing agent caused a 13.3 percent increase in yield.

What I claim is:

1. The process for this production of a succinylosuccinic acid diester which comprises reacting a γ-haloacetoacetic acid alkyl ester with a strong base (a), said reaction being conducted in an aqueous buffer solution of two inorganic slats or an inorganic salt and a strong inorganic base (b) at a pH of 8 to 10 in the presence of between 0.01 and 10 percent, based on the amount of said γ-haloacetoacetic acid alkyl ester, of a dispersing agent, said dispersing agent being selected from the group consisting of polyhydroxyethyl cellulose, an ammonium salt of a sulfate of an oxyethylated alkyl phenol, a sodium salt of a sulfate of an oxyethylated alkyl phenol, a fatty alcohol sulfate, an ethylene oxide propylene oxide copolymer, triethylbenzyl ammonium chloride, tetrabutyl ammonium iodide, dioctyldimethyl ammonium chloride, myristyldimethylbenzyl ammonium chloride tetraphenyl phosphonium chloride methoxymethyltriphenyl-phosphonium bromide, and said pH being kept constant, within said pH range, during said reaction by the addition of said strong inorganic base as meeded, said reaction being conducted at a temperature between -10° and 10° C., and said strong base (a) and said strong inorganic base (b) being the same or different and each having a dissociation constant in aqueous solution, of at least $1 \times 10^{-3}$.

2. The process of claim 1 wherein said dispersing agent is a polyhydroxyethyl cellulose.

3. The process of claim 1 wherein said dispersing agent is ammonium or sodium salt of a sulfate of an oxyethylated alkyl phenol.

4. The process of claim 1 wherein said dispersing agent is a fatty alcohol sulfate.

5. The process of claim 1 wherein said dispersing agent is an ethylene oxide propylene oxide copolymer.

6. The process of claim 1 wherein said dispersing agent is triethylbenzyl ammonium chloride.

7. The process of claim 1 wherein said dispersing agent is tetrabutyl ammonium iodide.

8. The process of claim 1 wherein said dispersing agent is dioctyldimethyl ammonium chloride.

9. The process of claim 1 wherein said dispersing agent is myristyldimethylbenzyl ammonium chloride.

10. The process of claim 1 wherein said dispersing agent is tetraphenyl phosphonium chloride.

11. The process of claim 1 wherein said dispersing agent is a methoxymethyltriphenylphosphonium bromide.

* * * * *